United States Patent
Chabrol et al.

(10) Patent No.: US 10,946,212 B2
(45) Date of Patent: Mar. 16, 2021

(54) IMPLANTABLE DEVICE FOR OPTICAL STIMULATION OF THE BRAIN

(71) Applicant: Commissariat à l'Energie Atomique et aux Energies Alternatives, Paris (FR)

(72) Inventors: Claude Chabrol, Poisat (FR); Alim-Louis Benabid, Meylan (FR)

(73) Assignee: Commissariat à l'Energie Atomique et aux Energies Alternatives, Paris (FR)

(*) Notice: Subject to any disclaimer, the term of this patent is extended or adjusted under 35 U.S.C. 154(b) by 130 days.

(21) Appl. No.: 16/063,258

(22) PCT Filed: Dec. 7, 2016

(86) PCT No.: PCT/FR2016/053248
§ 371 (c)(1),
(2) Date: Jun. 16, 2018

(87) PCT Pub. No.: WO2017/103380
PCT Pub. Date: Jun. 22, 2017

(65) Prior Publication Data
US 2019/0001149 A1    Jan. 3, 2019

(30) Foreign Application Priority Data
Dec. 17, 2015  (FR) ..................... 1562698

(51) Int. Cl.
*A61N 5/00* (2006.01)
*A61N 5/06* (2006.01)
*A61B 5/291* (2021.01)

(52) U.S. Cl.
CPC ......... *A61N 5/0622* (2013.01); *A61N 5/0601* (2013.01); *A61B 5/291* (2021.01);
(Continued)

(58) Field of Classification Search
CPC ..................... A61N 5/0622; A61N 2005/0612
(Continued)

(56) References Cited

U.S. PATENT DOCUMENTS 5,445,608 A  *  8/1995  Chen ................... A61N 5/0601
                                                            604/19
5,782,896 A     7/1998  Chen et al.
(Continued)

FOREIGN PATENT DOCUMENTS

FR      3010321 A1    3/2015
WO   2009155371 A1   12/2009

OTHER PUBLICATIONS

Written Opinion of the International Searching Authority for International Application No. PCT/FR2016/053248, dated Mar. 17, 2017, 4 pages.

(Continued)

*Primary Examiner* — Gary Jackson
*Assistant Examiner* — Anant A Gupta
(74) *Attorney, Agent, or Firm* — Moreno IP Law LLC

(57) ABSTRACT

The invention relates to an implantable device for optical stimulation of an organ of the human or animal body, having a probe comprising a tube made of a first transparent material, this tube being hermetically closed by at least one stopper; at least one light source arranged inside the tube; a plurality of electrical connection elements extending through the stopper and electrically connecting said at least one light source to the outside of the tube; and a linking cable arranged outside the tube and connected to said connection elements.

9 Claims, 1 Drawing Sheet

(52) U.S. Cl.
CPC .......................... *A61N 2005/063* (2013.01); *A61N 2005/0651* (2013.01); *A61N 2005/0659* (2013.01)

(58) Field of Classification Search
USPC .......................................................... 607/88
See application file for complete search history.

(56) References Cited

U.S. PATENT DOCUMENTS

| | | | |
|---|---|---|---|
| 8,634,918 B2* | 1/2014 | Chambers | A61N 1/378 607/36 |
| 2001/0003800 A1* | 6/2001 | Crowley | A61B 5/0059 607/88 |
| 2003/0016361 A1* | 1/2003 | Mank | H01L 51/5259 356/432 |
| 2009/0054955 A1* | 2/2009 | Kopell | A61N 5/0601 607/88 |
| 2009/0118800 A1 | 5/2009 | Deisseroth et al. | |
| 2015/0202456 A1* | 7/2015 | Andersen | A61N 1/0551 604/20 |
| 2015/0306415 A1* | 10/2015 | Tischendorf | A61N 5/0601 607/92 |
| 2017/0000419 A1* | 1/2017 | Schouenborg | A61B 5/0086 |

OTHER PUBLICATIONS

Kim et al., "Injectable, Cellular-Scale Optoelectronics with Applications for Wireless Optogenetics," Science, vol. 340, Apr. 13, 2013, pp. 211-216.

International Search Report for PCT/FR2016/052348 dated Mar. 17, 2017, 3 pages.

* cited by examiner

IMPLANTABLE DEVICE FOR OPTICAL STIMULATION OF THE BRAIN

CROSS-REFERENCE TO RELATED APPLICATION

Field

The present application concerns the field of implantable devices for the stimulation, by optical irradiation, of organs of the human or animal body, and particularly for deep optical brain simulation.

BACKGROUND

Deep brain stimulation is a therapeutic technique comprising the implantation in a patient's brain of a device enabling to stimulate specific portions of the brain. Treatments of certain neural dysfunctions, such as Parkinson's disease, by optical irradiation of brain portions with a light source emitting in Infrared, have in particular been provided.

Implantable devices enabling to implement treatments by deep optical irradiation of the brain by means of an optical fiber introduced into the patient's brain, via which light originating from a light source placed outside of the brain is guided towards the brain, have already been provided. An example of such a device is described in French patent application FR3010321 previously filed by the applicant.

The use of optical fibers however has limitations. In particular, an optical fiber only enables to illuminate a relative small surface area of the brain, due to the strong directivity of the light that it projects at its output. Further, coupling losses in the optical fiber compel to use an adapted light source (for example, laser, preferably with LEDs), which results in a relatively high electric power consumption of the device.

Another example of an implantable device enabling to implement treatments by optical irradiation is described in document U.S. Pat. No. 5,782,896.

It would be desirable to have a device for the deep optical irradiation of the brain, such a device overcoming all or part of the disadvantages of known devices.

SUMMARY

Thus, an embodiment provides an implantable device for the optical stimulation of an organ of the human or animal body, comprising a probe comprising a tube made of a first transparent material, the tube being hermetically closed by at least one cap; at least one light source arranged inside of the tube; a plurality of electric connection elements running through the cap and electrically coupling said at least one light source to the outside of the tube; and a connecting cable arranged outside of the tube, connected to said connection elements.

According to an embodiment, the device further comprises a sheath made of a second transparent material coating the tube and the cable.

According to an embodiment, the second material is an elastomeric material.

According to an embodiment, the first material is sapphire or silica.

According to an embodiment, the probe has an elongated shape, the tube being located at a first end of the probe and the connecting cable coupling the light source to a second end of the probe opposite to the first end.

According to an embodiment, the device further comprises a power supply and control unit electrically coupled to the light source via the connecting cable.

According to an embodiment, the light source comprises one or a plurality of light-emitting diodes.

According to an embodiment, the device further comprises a sensor capable of detecting a possible leakage in the tube.

According to an embodiment, the sensor comprises an organic light-emitting diode located inside of the tube.

According to an embodiment, the sensor further comprises a circuit for measuring a quantity representative of the impedance of the organic light-emitting diode and/or of the light efficiency of the organic light-emitting diode.

According to an embodiment, a transparent filling material is arranged inside of the tube.

According to an embodiment, the probe further comprises electrodes capable of implementing an electric stimulation of an organ of the human or animal body.

BRIEF DESCRIPTION OF THE DRAWINGS

The foregoing and other features and advantages will be discussed in detail in the following non-limiting description of specific embodiments in connection with the accompanying drawings, among which.

DETAILED DESCRIPTION OF THE PRESENT EMBODIMENTS

Figure 1:
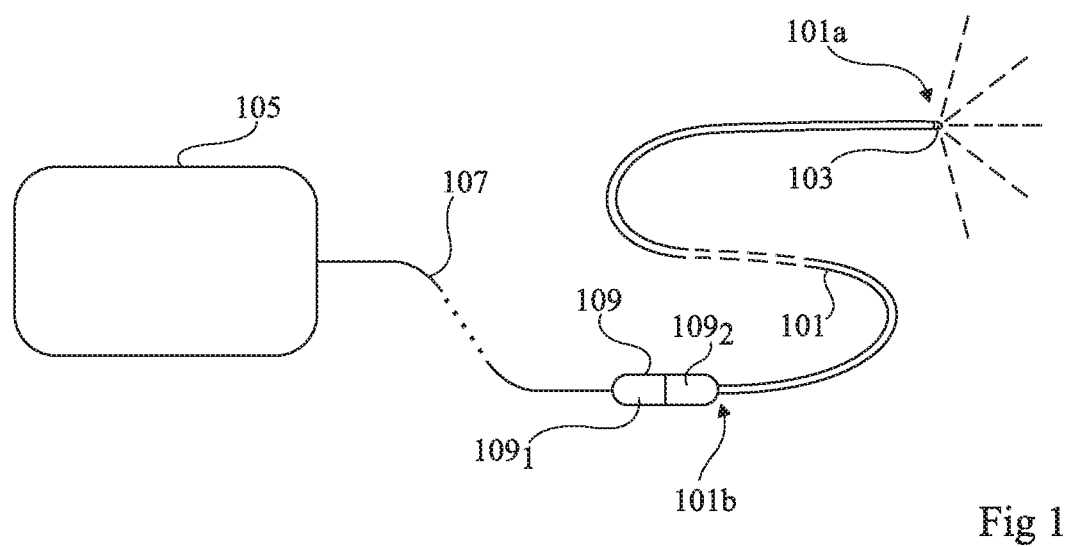
FIG. 1 is a simplified representation of an example of an embodiment of an implantable device for the optical irradiation of the brain.

The same elements have been designated with the same reference numerals in the different drawings and, further, the various drawings are not to scale. For clarity, only those elements which are useful to the understanding of the described embodiments have been shown and are detailed. The terms "approximately", "substantially", and "in the order of" are used herein to designate a tolerance of plus or minus 10%, preferably of plus or minus 5%, of the value in question.

FIG. 1 is a simplified representation of an embodiment of an implantable device for the optical irradiation of the brain. The device comprises an elongated probe 101 having a first end or distal end 101a intended to be implanted inside of the brain opposite a brain portion which is desired to be stimulated. Probe 101 for example has the general shape of a rod, for example, a rod having a circular cross-section. Probe 101 for example has the general shape and the dimensions of a DBS-type probe, which tool is currently used in the field of intra-cerebral implants. As an example, the width of probe 101 (that is, its diameter in the case of a rod having a circular cross-section) is in the range from 0.5 to 5 mm and preferably from 1.3 to 2.5 mm, and its length is in the range from 5 cm to 1 m and preferably from 15 to 30 cm. Probe 101 is preferably flexible to limit risks of lesion/damage of tissues. In practice, a rigid tool may be used for the surgical placement of the probe. Probe 101 comprises, on the side of its distal end 101a, a light source 103 capable of irradiating portions of the brain located opposite the distal end of the probe. Probe 101 further comprises a connecting cable (cable 225 of FIGS. 2 and 3, not shown in FIG. 1) electrically coupling light source 103 to a second end or proximal end 101b of the probe.

The device of FIG. 1 further comprises a unit 105 for powering and controlling light source 103, for example, comprising an electric battery and a control circuit capable of controlling light source 103 to implement desired stimulations of the brain. In the shown example, the device further comprises a cable 107 which couples unit 105 to proximal end 101b of probe 101. More particularly, the end of cable 107 opposite to unit 105 is electrically coupled or connected to the proximal end of probe 101, to enable unit 105 to power or to control source 103.

In practice, to minimize risks for the patient, only probe 101 is effectively implanted in the patient's brain, the other elements of the device being maintained outside of the brain for the entire duration of the treatment. As an example, the elements of the device of FIG. 1 other than probe 101 may be implanted in other parts of the patient's body. Power supply and control unit 105 may for example be implanted at the level of the patient's thorax. The coupling between cable 107 and probe 101 is preferably detachable or removable to be able to perform certain operations of maintenance of unit 105 or of cable 107 without having to extract probe 101 from the patient's brain. In the shown example, the coupling between cable 107 and probe 101 is performed via a connector 109, this connector comprising a portion $109_1$ solidly assembled with probe 107 and a portion $109_2$ solidly assembled with probe 101. Portions $109_1$ and $109_2$ of connector 109 are capable of detachably or removably cooperating to establish an electric connection between cable 107 and the connecting cable of probe 101. Connector 109 may for example be implanted under the scalp or in a housing previously burred into the patient's skull.

Figure 2:
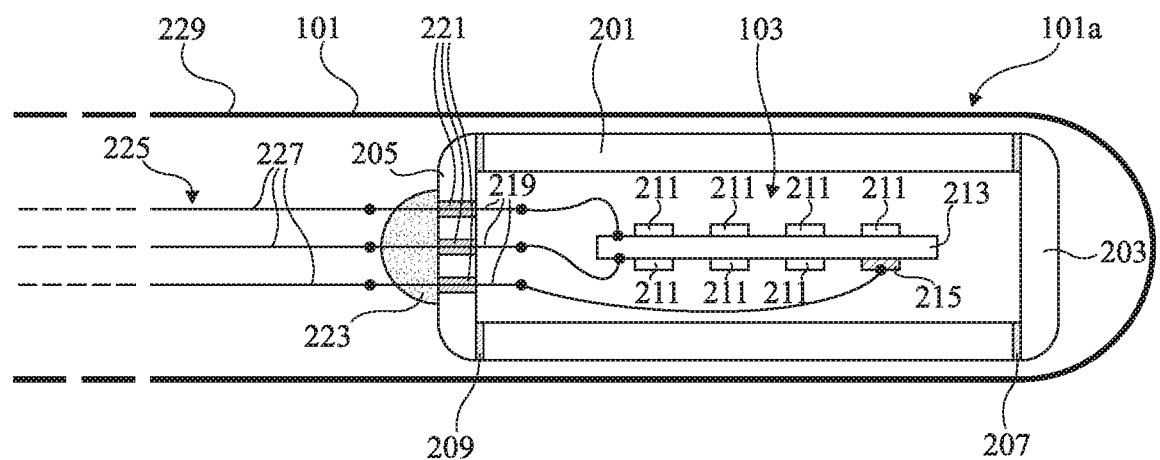
FIG. 2 illustrates in further detail a portion of the device of FIG. 1.

FIG. 2 shows in further detail an embodiment of probe 101 of the device of FIG. 1. FIG. 2 more particularly shows the distal portion of probe 101.

Probe 101 comprises, on the side of its distal end 101a, a tube 201 made of a transparent biocompatible material, for example sapphire or silica, having light source 103 arranged therein. Tube 201 for example has a circular cross-section. As an example, the width of tube 201 (that is, its diameter in the case of a tube having a circular cross-section) is in the range from 1 to 2 mm, and its length is in the range from 1 to 10 mm. Tube 201 is for example arranged so that its longitudinal central axis substantially coincides with the longitudinal central axis of the probe. Tube 201 may be made of a rigid material, for example, a material having a Young's modulus greater than 10 GPa. Transparent tube 201 is hermetically closed at its ends by caps 203 and 205. Caps 203 and 205 are for example (but not necessarily) transparent. Cap 203 may be integrated to tube 201 to form one piece with tube 201. As an example, caps 203 and 205 are made of the same transparent biocompatible material as tube 201 to ease the assembly, for example, by laser welding or metal soldering. In the shown example, cap 203 faces distal portion 101a of the probe, and cap 205 faces proximal portion 101b of the probe. Cap 203 is hermetically fastened all along its periphery to a first end of tube 201, for example, by welding, or by a hermetic biocompatible solder 207, for example, a gold solder. Cap 205 is hermetically fastened all along its periphery to a first end of tube 201, for example, by welding, or by a hermetic biocompatible solder 209, for example, a gold solder. The fastening of caps 203 and 205 to the ends of tube 201 is for example performed by thermosonic welding or by thermo-compression. Such methods have the advantage of being implementable at relatively low temperature, for example, at a temperature smaller than 200° C., which avoids damaging the components placed inside of tube 201. As a variation, the fastening of caps 203 and 205 to the ends of tube 201 is performed by laser welding through the material and with no added material. Once caps 203 and 205 are in place, the assembly comprising tube 201 and caps 203 and 205 forms a hermetic package capable of insulating all the non-biocompatible components that it contains, for example, a package having a helium leakage rate smaller than $10^{-6}$ atm·cm$^3$/s, preferably smaller than $10^{-8}$ atm·cm$^3$/s, with 1 atm=10,1325 Pa. As an example, the package is closed under a neutral atmosphere (oxygen-free), for example, under argon.

Prior to the hermetic closing of tube 201, the light source 103 of the probe is arranged inside of tube 201. The light source comprises one or a plurality of light emitters 211. Emitters 211 may be laser diodes, for example, vertical cavity surface emission laser (VCSEL) diodes, light-emitting diodes (LED), for example, organic light-emitting diodes (OLED), or any other adapted light sources. In the shown example, emitters 211 are assembled on a support 213, for example, a printed circuit board. Emitters 211 may for example be arranged on a same surface of a printed circuit board, or on the two opposite surfaces of a printed circuit board as shown in FIG. 2. Emitters 211 may be identical or similar and simultaneously controllable. As a variation, light source 103 comprises emitters 211 having different properties, for example, strips having different emission wavelengths. Further, the emitters 211 of light source 103 may be individually controllable. As an example, light source 103 comprises emitters 211 capable of emitting in a wavelength band in the range from 650 to 1,100 nm. More generally, any other emission wavelength range may be provided, for example, the range from 400 to 650 nm for optogenetics applications.

Probe 101 may further comprise, inside of tube 201, a sensor 215 capable of monitoring the hermeticity of the package formed by tube 201 and caps 203 and 205. In the shown example, sensor 215 is assembled on the same support 213 as the emitters 211 of light source 103. Hermeticity sensor 215 for example comprises a sensor of the inner pressure of tube 201, or a sensor of the humidity rate inside of tube 201.

As a variation, sensor 215 comprises one or a plurality of organic light-emitting diodes (OLED). Organic light-emitting diodes are indeed known to have a degraded performance in the presence of humidity or of oxygen. In this example, it is provided to measure characteristics of one or of a plurality of organic light-emitting diodes to detect the possible presence of oxygen or of humidity by abnormal proportions inside of the package formed by tube 201 and caps 203 and 205, and to deduce therefrom the presence of a leakage in the package. In particular, in the presence of humidity or of oxygen, the light efficiency of an organic light-emitting diode decreases relatively rapidly. Thus, sensor 215 may comprise an organic light-emitting diode and a photosensor capable of measuring the light intensity emitted by the diode. Power supply and control unit 105 may then be capable, based on the measurements supplied by the photosensor, of detecting a possible leakage in the package formed by tube 201 and caps 203 and 205. The impedance of an organic light-emitting diode is further known to increase relatively rapidly in the presence of humidity or of oxygen. Thus, sensor 215 may comprise an organic light-emitting diode, unit 105 being capable of measuring the impedance of this diode and of detecting, based on performed impedance measurements, a possible leakage in the package formed by tube 201 and caps 203 and 205. It should be noted that in the case where sensor 215 comprises an organic light-emitting diode, this diode may be used not only to monitor the hermeticity of the package formed by tube 201 and caps 203 and 205, but also as a light emitter for the optical irradiation of the patient's brain. In the case where sensor 215 comprises a photosensor, the latter may further be used to monitor the irradiation light signals emitted by emitters 211.

When unit 105 detects, based on the measurements supplied by sensor 215, a leakage in the package formed by tube 201 and caps 203 and 205, it for example triggers an alarm to notify that probe 101 should be replaced.

Probe 101 further comprises electric connection elements 219 running through the package formed by tube 201 and caps 203 and 205 and electrically coupling outside of the package the components located in tube 201. More particularly, probe 101 comprises at least two insulated electric connection elements 219 respectively coupled to a positive supply terminal and to a negative supply terminal of light source 103. Other connection elements 219 may further be provided to power the components located inside of tube 201 and/or for the communication with these components. In the shown example, each electric connection element 219 comprises a conductive rod thoroughly running through cap 205 via a hole or via pierced in the cap. Each of the vias is hermetically closed by a solder 221 made of a biocompatible material, for example, a gold solder. The outer portion of connection elements 219 may be totally or partially embedded in a resin drop 223 deposited on the outer surface of cap 205, to reinforce the mechanical resistance of the interconnection area. Electric connection elements 219 may be made of a biocompatible conductive material, for example of iridium-platinum.

Probe 101 further comprises, outside of tube 201, a connecting cable 225 electrically coupling connection elements 219 to the proximal end 101*b* of the probe. Cable 225 comprises a plurality of insulated conductive strands 227 respectively connected to the different connection elements 219. Strands 227 may be made of a biocompatible conductive material, for example, of stainless steel.

In the example of FIG. 2, probe 101 further comprises a protection sheath 229 made of a transparent biocompatible material coating tube 201 and connecting cable 227. Sheath 229 is for example made of a transparent elastomeric material, for example, of silicone or of polyurethane. As an example, sheath 229 is made of a material having a Young's modulus in the range from 1 to 1,000 MPa to provide flexibility to probe 101.

To limit parasitic reflections of the light emitted by source 103, the inner walls of tube 201 may be coated with an antireflection layer. As a variation, a transparent filling material having an adapted index, for example, a material having an index smaller than that of the material of tube 201, for example, silicone, may be injected inside of tube 201. The filling material may particularly be selected to have a heat conductivity greater than that of air. Thus, an additional advantage is that the presence of the filling material enables to improve the dissipation of the heat generated by the light source, and to accordingly increase the lifetime of the components.

An advantage of the device described in relation with FIGS. 1 and 2 lies in the fact that it enables to implement more varied optical stimulations of the brain than with an optical fiber device. In particular, the described device enables to irradiate larger surface areas of the brain than an optical fiber device. Further, light source 103 may comprise emitters 211 simultaneously emitting in different wavebands.

Further, the placing of the light source at the distal end of probe 101, that is, directly opposite the regions to be stimulated, enables to decrease the power of the light source and coupling losses (present in the case of a device comprising an offset source and an optical fiber), and accordingly the electric power consumption of the device with respect to an optical fiber device.

Another advantage of the device described in relation with FIGS. 1 and 2 is that the coating sheath may be arranged to give probe 101 a general shape and mechanical properties similar to those of existing electric deep brain stimulation devices, or to those of existing optical fiber deep brain stimulation devices. Thus, the implantation of probe 101 may be performed by means of tried and tested tools and surgical techniques. Further, this system remains compatible with standard stimulation control elements and the associated connectors.

Figure 3:
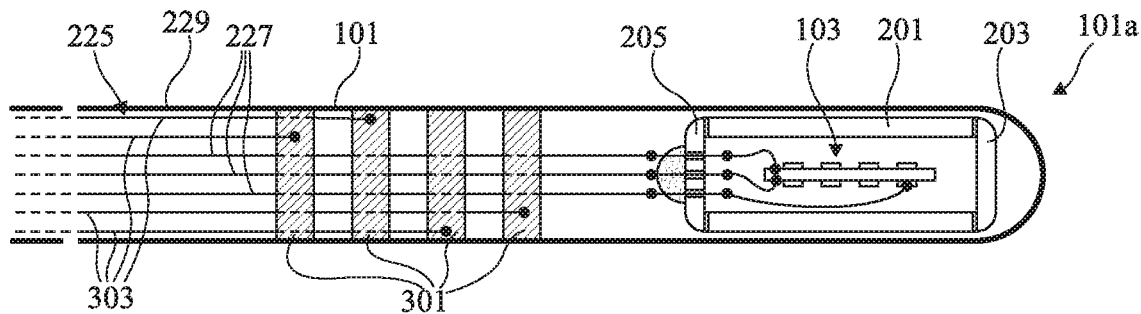
FIG. 3 shows an alternative embodiment of the device described in relation with FIGS. 1 and 2.

FIG. 3 shows an alternative embodiment of the device described in relation with FIGS. 1 and 2. FIG. 3 more particularly shows the distal portion of probe 101 of the device.

Probe 101 of FIG. 3 comprises the same elements as probe 101 of FIG. 2, arranged substantially in the same way. Probe 101 of FIG. 3 differs from probe 101 of FIG. 2 in that it further comprises, at the level of its distal portion, electrodes 301 (four in the shown example) capable of implementing a deep electric stimulation of the brain. Electrodes 301 are arranged on the outer periphery of sheath 229 and are intended to be placed directly in contact with the brain tissues. Electrodes 301 for example have the shape of rings surrounding sheath 229. Each electrode 301 for example has a width (that is, a distance along the longitudinal axis of probe 101) in the range from 0.5 to 3 mm, for example, in the order of 1 mm. The distance (along the longitudinal axis of probe 101) between two neighboring electrodes 301 is for example in the range from 0.2 to 2 mm, for example, in the order of 0.5 mm. Electrodes 301 are for example arranged upstream of the probe with respect to light source 103. As an example, the distance (along the longitudinal axis of probe 101) between light source 103 and the electrode 301 closest to light source 103 is in the range from 0.5 mm to 1 cm, for example, in the order of 1 mm. In the example of FIG. 3, the connecting cable 225 coupling the distal portion of probe 101 to its proximal end 101*b* further comprises insulated conductive strands 303 respectively connected to the different electrodes 301.

In the example of FIG. 3, control unit 105 (FIG. 1) of the device is not only capable of controlling light source 103 to implement optical stimulations of the brain, but is further capable of controlling electrodes 301 (via conductive strands 303) to implement electric stimulations of the brain, for example, simultaneously to the implementation of optical stimulations, or in alternation with the optical stimulations.

Specific embodiments have been described. Various alterations, modifications, and improvements will occur to those skilled in the art. In particular, the described embodiments are not limited to the above-mentioned examples of materials and dimensions.

Further, an embodiment where tube 101 is a tube initially open at its two ends, caps 203 and 205 being used to hermetically close the two ends of the tube, has been described herein. As a variation, tube 101 may be initially open at a single one of its ends, in which case a single cap may be used to close the tube.

Further, the described embodiments are not limited to the above-mentioned example of application to the deep irradiation of the brain. As a variation, the described devices may be used for the deep stimulation of organs of the human or animal body other than the brain.

What is claimed is:

1. An implantable device for optical stimulation of an organ of a human or animal body, comprising a probe comprising:
   a tube made of a first transparent material, the tube being hermetically closed by at least one cap;
   at least one light source arranged inside of the tube;
   a plurality of electric connection elements running through the at least one cap and electrically coupling said at least one light source outside of the tube;
   a connecting cable arranged outside of the tube, connected to said connection elements;
   a sensor configured for detecting a possible leakage in the tube, the sensor comprising an organic light-emitting diode located inside the tube; and
   a sheath made of a second transparent material coating the tube and the cable.

2. The device of claim 1, wherein the second material is an elastomeric material.

3. The device of claim 1, wherein the first material is sapphire or silica.

4. The device of claim 1, wherein the probe has an elongated shape, the tube being located at a first end of the probe and the connecting cable coupling the at least one light source to a second end of the probe opposite to the first end.

5. The device of claim 1, further comprising a power supply and control unit electrically coupled to the at least one light source via the connecting cable.

6. The device of claim 1, wherein the light source comprises one or a plurality of light-emitting diodes.

7. The device of claim 1, wherein said sensor further comprises a circuit for measuring a quantity representative of impedance of the organic light-emitting diode and/or of light efficiency of the organic light-emitting diode.

8. The device of claim 1, wherein a transparent filling material is arranged inside of the tube.

9. The device of claim 1, wherein the probe further comprises electrodes capable of implementing an electric stimulation of an organ of the human or animal body.

* * * * *